United States Patent
Rogers et al.

(10) Patent No.: US 7,381,950 B2
(45) Date of Patent: Jun. 3, 2008

(54) CHARACTERIZING DIMENSIONS OF STRUCTURES VIA SCANNING PROBE MICROSCOPY

(75) Inventors: Duncan M. Rogers, Plano, TX (US); Vladimir A. Ukraintsev, Allen, TX (US)

(73) Assignee: Texas Instruments Incorporated, Dallas, TX (US)

(*) Notice: Subject to any disclaimer, the term of this patent is extended or adjusted under 35 U.S.C. 154(b) by 138 days.

(21) Appl. No.: 10/953,629

(22) Filed: Sep. 29, 2004

(65) Prior Publication Data
US 2006/0071164 A1    Apr. 6, 2006

(51) Int. Cl.
*H01J 37/28* (2006.01)
(52) U.S. Cl. ............................. 250/307; 73/105; 702/85
(58) Field of Classification Search ................ 250/306, 250/307, 492.2; 73/105; 324/754, 761, 324/762; 702/85, 170, 150, 155
See application file for complete search history.

(56) References Cited

U.S. PATENT DOCUMENTS

| | | | | |
|---|---|---|---|---|
| 5,155,359 A | * | 10/1992 | Monahan | 250/306 |
| 5,835,477 A | * | 11/1998 | Binnig et al. | 369/126 |
| 5,905,573 A | * | 5/1999 | Stallard et al. | 356/519 |
| 6,005,669 A | * | 12/1999 | Pahk et al. | 356/602 |
| 6,789,033 B2 | * | 9/2004 | Solecky et al. | 702/85 |
| 7,173,314 B2 | * | 2/2007 | Adelmann | 257/415 |
| 2005/0012936 A1 | * | 1/2005 | Murayama et al. | 356/601 |
| 2005/0283335 A1 | * | 12/2005 | Banke et al. | 702/170 |

* cited by examiner

*Primary Examiner*—Kiet T Nguyen
(74) *Attorney, Agent, or Firm*—Rose Alyssa Keagy; W. James Brady, III; Frederick J. Telecky, Jr.

(57) ABSTRACT

A method comprising characterizing the dimensions of structures on a semiconductor device having dimensions less than approximately 100 nanometers (nm) using one of scanning probe microscopy (SPM) or profilometry.

9 Claims, 1 Drawing Sheet

CHARACTERIZING DIMENSIONS OF STRUCTURES VIA SCANNING PROBE MICROSCOPY

BACKGROUND

Integrated circuits are fabricated on the surface of a semiconductor wafer in layers, and later singulated into individual semiconductor devices, or "dies." Many fabrication processes are repeated numerous times, constructing layer after layer until fabrication is complete. Metal layers, which typically increase in number as device complexity increases, include patterns of conductive material that are vertically insulated from one another by alternating layers of insulating material. Conductive traces are also separated within each layer by an insulating, or dielectric, material. Vertical, conductive tunnels called "vias" typically pass through insulating layers to form conductive pathways between adjacent conductive patterns.

Advancements in the size and speed of semiconductor devices continue to occur in order to meet consumer and competitive demands. The reduction in size of device features that accompanies such advancements also pushes innovation in the capabilities of manufacturing tools. Particularly, measurement techniques and tools must be able to accurately detect smaller and smaller dimensions.

SUMMARY

The problems noted above are solved in large part by a method for characterizing dimensions of structures by way of scanning probe microscopy. An exemplary embodiment comprises a method comprising characterizing the dimensions of structures on a semiconductor device having dimensions less than approximately 100 nanometers (nm) using one of scanning probe microscopy (SPM) or profilometry. Another exemplary embodiment comprises a method comprising establishing a reference position on a semiconductor device using one of SPM or profilometry, establishing a target position on an upper surface of the structure using one of SPM or profilometry, said upper surface facing away from the device. The method further comprises determining the difference between the reference position and the target position, wherein the reference position and the portion of the device coupled to the structure are coplanar.

BRIEF DESCRIPTION OF THE DRAWINGS

For a detailed description of exemplary embodiments of the invention, reference will now be made to the accompanying drawings in which.

NOTATION AND NOMENCLATURE

Figure 1A:
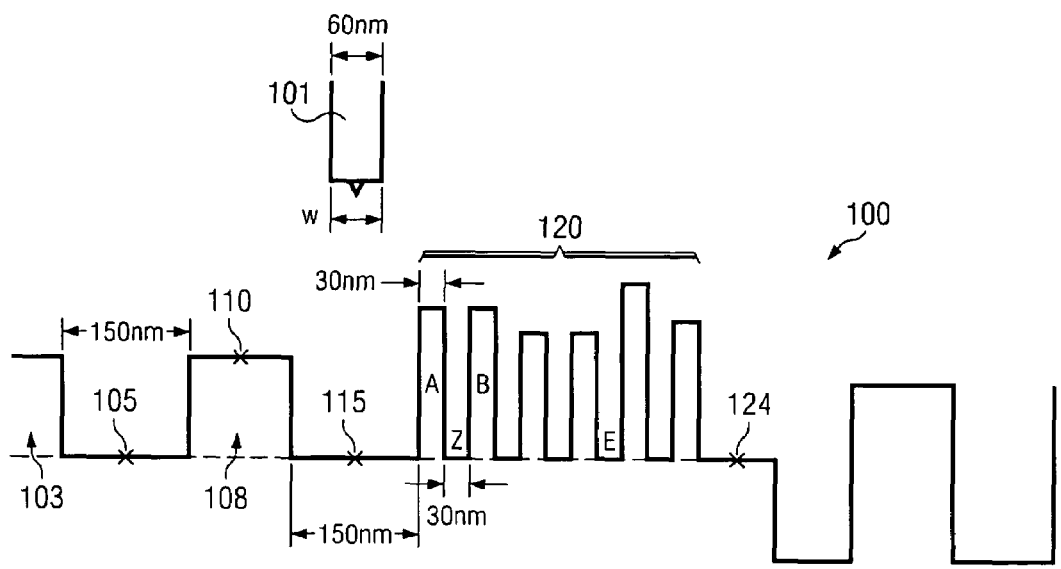
FIG. 1a shows a cross-sectional side view of a semiconductor device surface comprising multiple sub-100 nm structures, in accordance with embodiment of the invention.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

The term "integrated circuit" or "IC" refers to a set of electronic components and their interconnections (internal electrical circuit elements, collectively) that are patterned on the surface of a microchip. The term "semiconductor device" refers generically to an integrated circuit (IC). The term "die" ("dies" for plural) refers generically to an integrated circuit or semiconductor device, which may be a portion of a wafer, in various stages of completion, including the underlying semiconductor substrate, insulating materials, and all circuitry patterned thereon. The term "trench" refers generically to any feature that adds a dimension among the materials forming a die. To the extent any term is not specifically defined in this specification, the intent is that the term be given its plain and ordinary meaning.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Provided herein are methods of characterizing the dimensions of structures on semiconductor devices, such as integrated circuits (IC), via scanning probe microscopy (SPM) and/or profilometry, where a device comprises structures having dimensions less than about 100 nanometers. While the measurement techniques disclosed herein are primarily discussed in context of SPM, any technique, such as profilometry, also may be used. In accordance with various embodiments, the dimensions of structures are characterized by reckoning the distance from a probe of the SPM at a reference position to the probe of the SPM at a second position. The reference position may be represented by a single measurement, an average of multiple measurements, or a range of measurements taken at one or more positions designed to be in the same plane.

SPM permits the imaging and measuring of surfaces on a fine scale (e.g., on the scale of several microns), even to the level of molecules and/or groups of atoms. A variety of SPM techniques exist and may be used in context of the subject matter presented below. Such techniques include, among others, atomic force microscopy (AFM), scanning tunneling microscopy (STM), and near-field scanning optical microscopy (NSOM). Specifically, AFM measures the interaction force between a tip of the probe and a surface that is to be measured. The tip may be dragged across the surface, or may vibrate as it moves. The interaction force will depend on the nature of the sample, the probe tip and the distance therebetween. STM measures a weak electrical current flowing between tip and sample as they are held apart from each other. NSOM scans a light source that is located in substantially close proximity to the sample. Detection of this light energy is used to form images or measurements. NSOM can provide resolution below that of the conventional light microscope. The scope of disclosure is not limited to these types of SPM. SPM is described in greater detail in U.S. Pat. No. 5,371,365, which is incorporated herein by reference.

FIG. 1a illustrates an example of a cross-sectional view of a surface 100 exhibiting structures of varying dimensions. A SPM probe 101 may be employed to characterize the dimensions of the structures on the surface 100. The height of structure 108, for example, may be characterized by reckoning the distance from a SPM probe measurement taken at position 105 to a SPM probe measurement taken at a second position 110. The probe 101, in this illustration having a width of 60 nm, may be placed at position 105 between structures 103 and 108 as the distance between structures 103 and 108 is 150 nm.

The probe 101 may also be employed to characterize the dimensions of a series of structures 120 having dimensions smaller than the probe 101. The structures in the series 120, such as structure A and structure B, are 30 nm wide and divided by distances of 30 nm. Thus, the 60 nm probe 101 will not reach position Z, for example, in order to characterize the dimensions the structures in the series 120. In embodiments, the SPM probe 101 scans the surface 100 in order to create a profile of the structures. Where the probe 101 will not reach certain positions, such as position Z among the series of structures 120 having dimensions smaller than the probe, it may scan the contour of the series 120 in order to create a profile of the contour of the series 120. Such a profile of the surface 100 is illustrated in FIG. 1b.

Figure 1B:
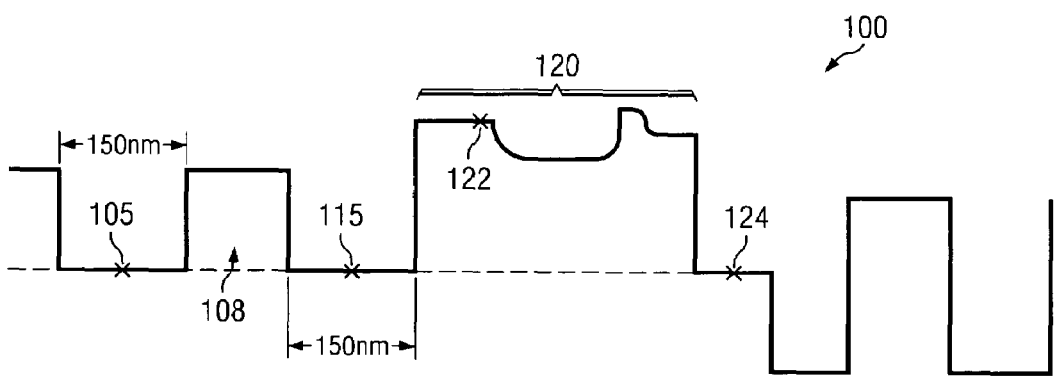
FIG. 1b shows the configuration of FIG. 1a, wherein the surfaces of the sub-100 nm structures are shown as a continuous contour, in accordance with embodiments of the invention.

FIG. 1b illustrates what may result from a scan of the surface 100 in FIG. 1a with an SPM probe. The probe scan takes measurements at positions it may reach to create an outline of the structures on the surface 100. Thus, a scan of the series of structures 120 outlines the contour 122 of the series 120.

The dimensions of the structures in the series 120 may be characterized by establishing a reference position. The surface 100 may be designed such that positions 115, Z, and E, for example, are all designed to be in the same plane. In such a case, position 115 may be a reference position for characterizing the dimensions, e.g. heights, of structures in series 120 where a larger probe 101 will not reach. The reference position may comprise any position having dimensions that permit access by the SPM probe.

Thus, in various embodiments, by establishing a reference position, a SPM probe may characterize the dimensions of structures, including sub-100 nm structures, on a surface 100 that includes structures having dimensions smaller than the probe 101. Measurements for such characterizations may be accomplished independent of the size of the SPM probe. Such SPM probes may comprise a tip size less than or equal to about 1000 nm in diameter. The probe may scan a surface 100 to outline the contour 122 of the surface 100, such as illustrated by FIGS. 1a and 1b. Positions 105 and 115, accessible by probe 101 and designed to be in the same plane as positions not accessible by probe, such as position Z and position E, may be used to establish a reference position. In some embodiments, the reference position comprises an average of measurements at positions designed to be in the same plane. For example, where positions 105, 115, and 124 are designed to be in the same plane, the reference position for characterizing the dimensions of structures not accessible by probe may be established by averaging probe measurements taken at positions 105, 115, and 124.

The various heights of structures among the series 120 may be characterized by reckoning the distance from the height of the probe at the established reference position to the height of the probe at the various positions along the contour 122.

Figure 2:
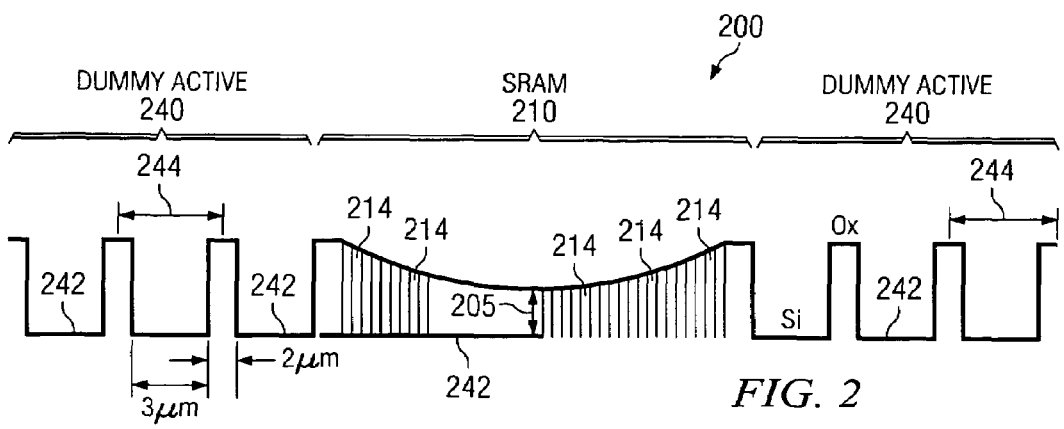
FIG. 2 shows a cross-sectional side view of a SRAM array on a surface of a semiconductor device, in accordance with embodiments of the invention.

In some embodiments, characterizing the dimensions of structures comprises measuring step height in an SRAM array. In other embodiments, structures that may be characterized by the method provided comprise DRAM, Logic, inductors, input/output structures, or combinations thereof. FIG. 2 illustrates a surface 200 of a cross-sectional view of an SRAM array 210 on a section of a semiconductor device, which includes sub-100 nm structures, and the surrounding dummy active region 240. The field oxide of the SRAM 210 may contain many structures with dimensions smaller than the smallest SPM probe, e.g., 10 nm structures 214. In this example, a distance 244 between at least some oxides may be approximately 3 micrometers.

The step height 205 of the SRAM may be defined as the difference between the height of a SPM probe when scanning the surface 242 of the dummy active region 240, and the height of the SPM probe when scanning the surface contour of the SRAM 210 field oxide. The SPM probe may scan the surface of the dummy active region 240 in order to establish the height of the SPM probe at the surface of the dummy active 242 as the reference position. The device may be designed such that the base of the SRAM is the same height as the surface of the dummy active. The SPM probe may also scan the surface of the SRAM 210 in order to outline the contour of the structures 214 of the field oxide. The scan of the contour of the field oxide region may capture variations in the height of the structures 214.

The difference between height of the SPM probe at the reference position(s) 242 and the height(s) of the SPM probe along the contour of the SRAM 210 and its structures 214 may provide the step height 205 of the SRAM 210. In addition, such characterization may indicate the range of heights of structures 214 in the SRAM 210. In some embodiments, measuring the height of the SPM probe at one or more positions on the dummy active 242 establishes a reference position or average reference position. In other embodiments, establishing a reference position at multiple points on a wafer may be used to indicate the variation in step height across a wafer.

In various embodiments, the method provided may be employed to characterize the dimensions of structures on a semiconductor device comprising sub-100 nm structures via SPM in less than or equal to about 1 hour. Specifically, the SPM probe is able to scan the surface contour of the SRAM 210 without measuring the SRAM step height between each oxide structure. That is, instead of making several time-consuming measurements to repeatedly determine step height, only a few measurements are made and the step height is thereafter determined by calculation. Thus, in some situations, using SPM to characterize the dimensions of structures on a device comprising sub-100 nm structures may require less than 20 seconds.

While various embodiments of the invention have been shown and described, modifications thereof can be made by one skilled in the art without departing from the spirit and teachings of the invention. The techniques disclosed herein may be applied to any semiconductor device, such as an integrated circuit. The embodiments described herein are exemplary only, and are not intended to be limiting. Equivalent techniques and ingredients may be substituted for those shown, and other changes can be made within the scope of the present invention as defined by the appended claims. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

What is claimed is:

1. A method comprising characterizing the physical height of structures on a semiconductor device having dimensions less than approximately 100 nanometers (nm) using a probe of one of scanning probe microscopy (SPM) and profilometry by determining the difference in height between the probe of one of a SPM and profilometer at a reference position to the probe at a second position.

2. The method of claim 1 wherein the reference position comprises an average of measurements at positions designed to be in the same plane.

3. The method of claim 1 wherein the reference position comprises any position having dimensions that permit access by the probe.

4. The method of claim 1 wherein said structures are selected from a group consisting of static random access memory (SRAM) arrays, dynamic random access memory (DRAM) arrays, inductors, input/output structures, and combinations thereof.

5. The method of claim 1 wherein characterizing the height of structures comprises measuring step height in a static random access memory (SRAM) array.

6. The method of claim 5 wherein measuring step height in an SRAM array comprises determining the distance from the one of a SPM probe and profilometer probe at a dummy active to the one of a SPM probe and profilometer probe on a SRAM field oxide.

7. The method of claim 1 wherein the device has dimensions between approximately 0.2 nm and 100 nm.

8. The method of claim 1 wherein a space between adjacent structures is less than a width of the probe.

9. The method of claim 1 wherein the reference position is in the same plane as a lowest point of the structure and at least one structure separates the reference position from the structure being characterized.

* * * * *